United States Patent
Shang et al.

(10) Patent No.: US 11,532,919 B2
(45) Date of Patent: Dec. 20, 2022

(54) FRACTIONAL HANDPIECE WITH A PASSIVELY Q-SWITCHED LASER ASSEMBLY

(71) Applicant: Candela Corporation, Marlborough, MA (US)

(72) Inventors: Xiaoming Shang, Lexington, MA (US); Hui Liu, Boston, MA (US); Craig Langlois, Clinton, MA (US); Kevin Schomacker, Maynard, MA (US)

(73) Assignee: CANDELA CORPORATION, Marlborough, MA (US)

( * ) Notice: Subject to any disclaimer, the term of this patent is extended or adjusted under 35 U.S.C. 154(b) by 295 days.

(21) Appl. No.: 16/884,708

(22) Filed: May 27, 2020

(65) Prior Publication Data
US 2021/0376553 A1    Dec. 2, 2021

(51) Int. Cl.
*H01S 3/11* (2006.01)
*G02B 27/14* (2006.01)
(Continued)

(52) U.S. Cl.
CPC .......... *H01S 3/1115* (2013.01); *A61N 5/0616* (2013.01); *G02B 5/001* (2013.01);
(Continued)

(58) Field of Classification Search
CPC .... H01S 3/1115; H01S 3/0014; H01S 3/0625; H01S 3/1611; H01S 3/094076; H01S 3/0071; H01S 3/0621; H01S 3/0627; H01S 3/09415; H01S 3/113; A61N 5/0616; A61N 5/067; A61N 2005/0644; G02B 5/001; G02B 27/106; G02B 27/14; G02B 27/4233; G02B 26/0816; G02B 26/105; G02B 26/101; G02B 26/0808; G02B 27/0927; G02F 1/37; A61B 2017/00075; A61B 2018/00303; A61B 2018/0047; A61B 2018/00642; A61B 2018/0066; A61B 2018/00702; A61B 2018/00708;
(Continued)

(56) References Cited

U.S. PATENT DOCUMENTS 4,447,723 A * 5/1984 Neumann ................ H04N 1/12
                                                   250/236
5,394,413 A * 2/1995 Zayhowski ........... H01S 3/0627
                                                    372/21
(Continued)

OTHER PUBLICATIONS

Butler, et al., Scaling Q-switched microchip lasers for shortest pulses, applied Physics B, Lasers and Optics, Springer, Berlin, DE, vol. 109, No. 1 pp. 81-88, Sep. 22, 2012.
(Continued)

*Primary Examiner* — Xinning(Tom) Niu
(74) *Attorney, Agent, or Firm* — Polsinelli PC

(57) ABSTRACT

A fractional handpiece and systems thereof for skin treatment include a passively Q-switched laser assembly operatively connected to a pump laser source to receive a pump laser beam having a first wavelength and a beam splitting assembly operable to split a solid beam emitted by the passively Q-switched laser assembly and form an array of micro-beams across a segment of skin. The passively Q-switched laser assembly generates a high power sub-nanosecond pulsed laser beam having a second wavelength.

21 Claims, 15 Drawing Sheets

(51) Int. Cl.
*H01S 3/06* (2006.01)
*H01S 3/16* (2006.01)
*G02B 5/00* (2006.01)
*G02B 27/42* (2006.01)
*H01S 3/00* (2006.01)
*A61N 5/06* (2006.01)
*G02B 27/10* (2006.01)
*H01S 3/094* (2006.01)
*G02F 1/37* (2006.01)
*G02B 26/08* (2006.01)
*G02B 26/10* (2006.01)
*A61N 5/067* (2006.01)

(52) U.S. Cl.
CPC ............ *G02B 27/106* (2013.01); *G02B 27/14* (2013.01); *G02B 27/4233* (2013.01); *H01S 3/0014* (2013.01); *H01S 3/0625* (2013.01); *H01S 3/1611* (2013.01); *A61N 5/067* (2021.08); *A61N 2005/0644* (2013.01); *G02B 26/0816* (2013.01); *G02B 26/105* (2013.01); *G02F 1/37* (2013.01); *H01S 3/094076* (2013.01)

(58) Field of Classification Search
CPC .. A61B 2018/00898; A61B 2018/0091; A61B 2018/20359; A61B 2018/20553; A61B 2018/205547; A61B 2018/208; A61B 18/203
See application file for complete search history.

(56) References Cited

U.S. PATENT DOCUMENTS

| | | | |
|---|---|---|---|
| 5,966,392 A * | 10/1999 | Chen | H01S 3/0627 372/75 |
| 2009/0057409 A1* | 3/2009 | Feinstein | G06K 7/10633 235/462.02 |
| 2009/0227995 A1* | 9/2009 | Bhawalkar | A61B 18/20 606/9 |
| 2009/0254073 A1* | 10/2009 | Davenport | A61B 18/203 606/18 |
| 2017/0133815 A1 | 5/2017 | Kopf | |
| 2017/0358898 A1 | 12/2017 | Taira et al. | |

OTHER PUBLICATIONS

International Search Report and Provisional Opinion in PCT/US2019/037418 dated Jun. 17, 2019, 18 pages.

* cited by examiner

FRACTIONAL HANDPIECE WITH A PASSIVELY Q-SWITCHED LASER ASSEMBLY

FIELD

The present system relates to a passively Q-switched laser packaged in a handpiece and in particular to laser systems with a fractional handpiece with a passively Q-switched laser assembly and a beam splitting assembly.

BACKGROUND

Typically, systems for non-invasive treatment of skin disorders include a cabinet into which a laser is placed and a beam delivery system (typically an optical fiber or an articulated arm) connected to a handpiece that conducts the laser radiation from the laser to a segment of skin to be treated. The functionality of such a system is limited by the capabilities of the selected laser. Treatment of skin imperfections usually requires more than one type of laser and frequently more than one type of laser is placed in the cabinet. This increases size, cost and complexity of the system.

Treatment of some skin imperfections requires significant laser power (tens and even hundreds of MW) that in order to prevent skin damage is supplied in ultrashort pulses (most commonly in picosecond regime). Such laser power is difficult to transfer through a fiber and use of an articulated arm significantly limits the freedom of the caregiver.

A typical Q-switched microcavity laser consists of a laser medium and a saturable absorber as a passive Q-switcher positioned very close each other. The cavity length is managed to be as short as possible. Q-switched microcavity lasers are small solid-state lasers with linear short cavity. The typical cavity length is on the order of millimeter. The short cavity lengths result in extremely short cavity lifetimes, and the possibility of much shorter Q-switched pulses. It has been demonstrated that Q-switched microcavity lasers can produce output pulses on a subnanosecond regime. In some special cases (i.e., monolithic cavity), the pulse duration can be, as short as large mode-locked lasers produce with peak powers of about 10 KW, similar to commercially available large Q-switched systems produce.

Over decades, a lot of effort has been put in places striving for generation of high energy picosecond lasers. Many techniques have been developed. These techniques commonly involve multi-stage configurations, i.e., a low energy picosecond seed laser, for example nJ or µJ are fed into amplification stages (including regenerative amplifier or/and multi-pass amplifications). Such multi-stage configurations require complex optical arrangement and sophisticated electronic synchronization further increasing the complexity and cost of the system.

BRIEF DESCRIPTION OF THE DRAWINGS

The patent or application file contains at least one drawing executed in color. Copies of this patent or patent application with color drawing(s) will be provided by the Office by request and payment of the necessary fee.

For a more complete understanding of this disclosure and its features, reference is now made to the following description, taken in conjunction with accompanying drawings, in which like reference numerals denote like elements.

DETAILED DESCRIPTION

Figure 1:
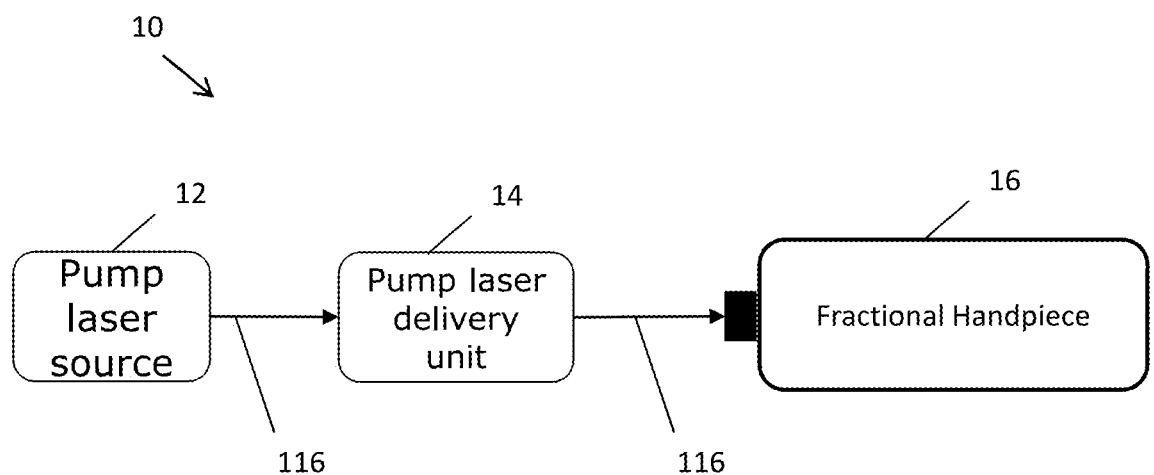
FIG. 1 is an example of a system having a pump source, pump laser delivery unit, and a subnanosecond fractional handpiece.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. The terms "comprising," "including" and "having" are used interchangeably in this disclosure. The terms "comprising," "including" and "having" mean to include, but not necessarily be limited to the things so described.

Disclosed herein is a system having a subnanosecond fractional handpiece with a passively Q-switched laser assembly and a method to implement the fractional handpiece. As shown in FIG. 1, the system 10 may include a pump laser source 12, a pump laser delivery unit 14, and the fractional handpiece 16.

In an example, the pump laser source 12 may be located in a cabinet. The pump laser source 12 may be any pump laser operable to provide energy to start the passively Q-switched laser in the handpiece to generate high energy (>1 mJ) short pulses in a subnanosecond regime. For example, the pump laser may be operable to generate picosecond laser pulses with high peak power of about 100 MW and higher when used in combination with the fractional handpiece. The pump laser source may be a laser emitting wavelength at which the laser rod has enough absorption. For example, for an Nd:YAG laser, the pump laser wavelength may be within one of three wavelength bands, i.e., 735-760 nm, 795-820 nm, or 865-885 nm. The pump laser may be a solid state laser or diode laser. Non-limiting examples of pump lasers include an Alexandrite laser (755 nm), a Ti:Sapphire laser, a diode laser, a dye laser, an optical parametric oscillator (OPO), and an optical parameter amplifier (OPA). Ti:Sapphire may be used to generate laser beams in the wavelength range between 700-900 nm via direct emission pumped in the visual wavelength region. In an example, an Alexandrite laser may provide over 1 kW pumping power for higher pulse energy generation. The high pumping power facilitates energy storage that is further facilitated by use of a saturable absorber of low initial transmission.

The pump laser delivery unit 14 may be operable to deliver the pump laser to the fractional handpiece for pumping the passively Q-switched laser. In some examples, the pump laser delivery unit may be an articulated arm which is an assembly of a number of mirrors and mechanical levers or arms connected between them by rotary joints. In an example, the articulated arm may have a plurality of arms (elbows) and a plurality of mirrors operable to direct the laser beam to a desired point on the fractional handpiece by rotation around at least one rotary joint connecting the plurality of arms. In an example, the plurality of mirrors is operable to preserve incident laser beam polarization, which may be useful for efficient pumping of anisotropic laser material (i.e., Nd:YAP and Nd:YLF). In additional examples, the pump laser delivery unity may include fiber optics and be delivered by an optical fiber. The optical fiber may a single mode fiber, multimode fiber, or hollow core fiber.

Figure 2A:
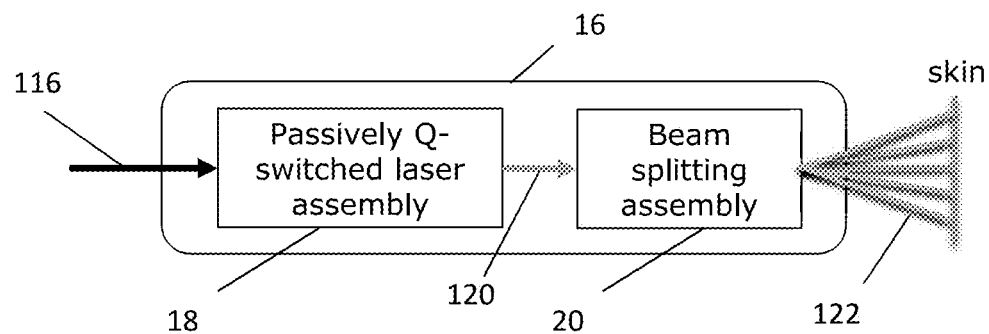
FIG. 2A is an example of a fractional handpiece with a passively Q-switched laser assembly and a beam splitting assembly.

As seen in FIG. 2A, the fractional handpiece 16 may include a passively Q-switched laser assembly 18 and a beam splitting assembly 20. The fractional handpiece is operable to generate high energy (>10 mJ) subnanosecond laser pulses and subsequently deliver those pulses to treatment sites (i.e., the skin) with a fractionated pattern. The fractional handpiece receives the pump laser delivered by the pump laser delivery unit to pump the passively Q-switched laser to generate high energy (>10 mJ) subnanosecond pulses. The generated subnanosecond laser is then split by the beam splitting assembly into a microdot array that is delivered to the skin for fractional treatment.

The dimensions of the passively Q-switched laser assembly allow it to be contained and mounted within the fractional handpiece body thereby reducing the size and complexity of the total system and improving the power utilization efficiency. The fractional handpiece may then be used in different applications and in particular for skin disorders treatment. The fractional handpiece body may be of a reasonable size and weight that easily fits within a user's hand and may be carried with a hand. The fractional handpiece may be less than or equal to 35 cm in length. In at least one example, the handpiece body may have a shape that facilitates it being held like a pencil. In other examples, the handpiece body may include a pistol grip that facilitates the handpiece body being held like a pistol.

Figure 2B:
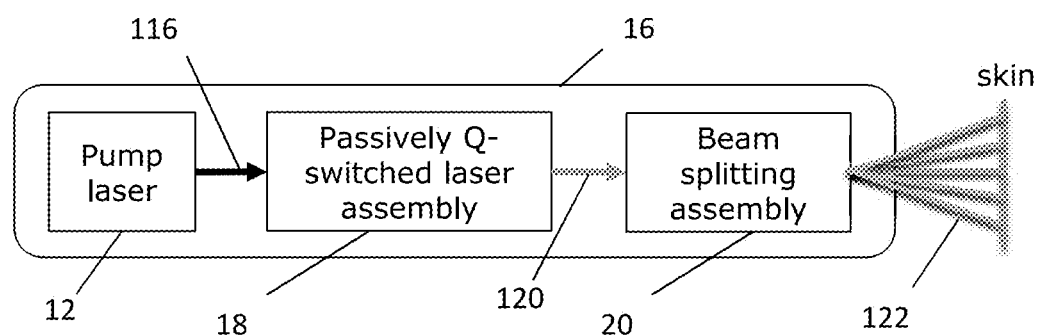
FIG. 2B is an example of a fractional handpiece with a pump laser source, a passively Q-switched laser assembly, and a beam splitting assembly.

In some examples, as seen in FIG. 2B, the pump laser source 12 and/or the pump laser delivery unit may also be small enough in size to be contained within the fractional handpiece body 16. In at least one example, the pump laser source 12 may be a diode laser may be located within the fractional handpiece body and is operable to directly illuminate the passively Q-switched laser assembly.

Figure 2C:
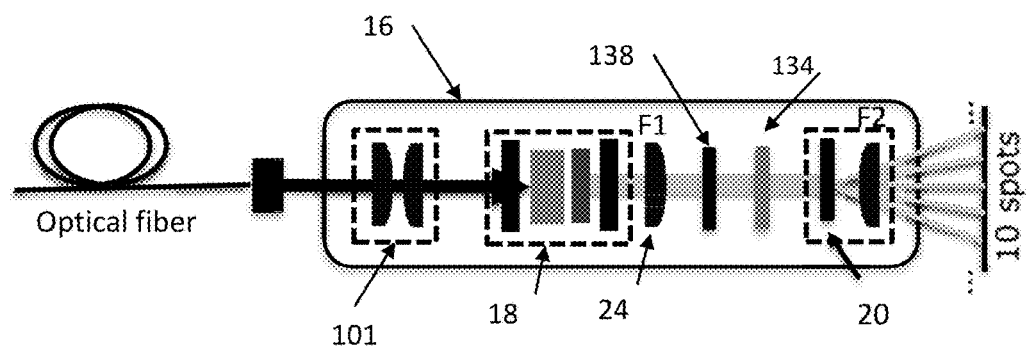
FIG. 2C is an example 1064 nm handpiece.
Figure 2D:
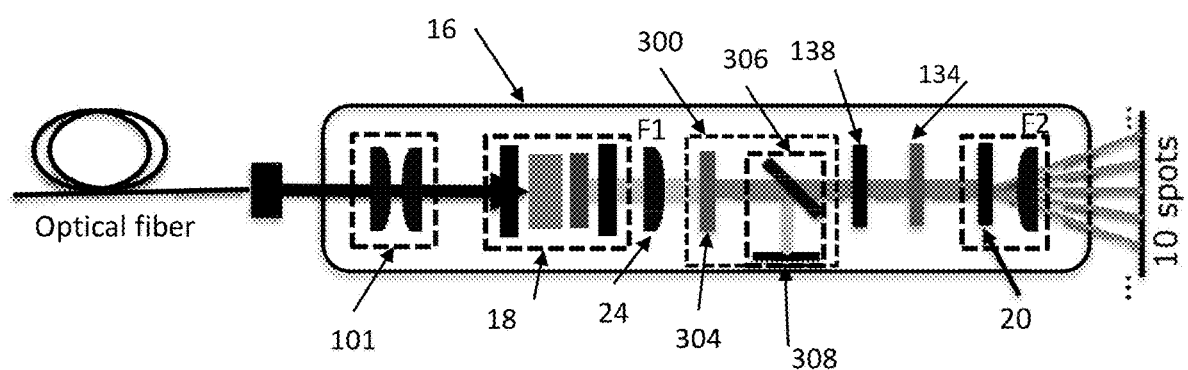
FIG. 2D is an example 532 nm handpiece.

FIG. 2C shows an example 1064 nm handpiece and FIG. 2D shows an example 532 nm handpiece, each using an optical fiber pump laser deliver unit. The fractional handpiece 16 in FIG. 2C includes pump lenses 101, a seed cavity with a passively Q-switched laser assembly 18, a collimating lens 24, a homogenizer 134, an attenuator 138, and a 1-D beam splitting assembly 20. The fractional handpiece 16 in FIG. 2D includes pump lenses 101, a seed cavity with a passively Q-switched laser assembly 18, a collimating lens 24, a second harmonic generation assembly 300, a homogenizer 134, an attenuator 138, and a 1-D beam splitting assembly 20.

The passively Q-switched laser assembly emits subnanosecond pulses at a laser power of tens and hundreds of MW. The passively Q-switched laser assembly does not require switching electronics, thereby reducing the size and complexity of the total system and improving the power efficiency. In addition, there is no need for interferometric control of the cavity dimensions, simplifying production of the device and greatly relaxing the tolerances on temperature control during its use. The result is a potentially less expensive, smaller, more robust, and more reliable Q-switched laser system with performance comparable with that of the coupled cavity Q-switched laser. The compact short cavity passively Q-switched laser assembly may be used for a large range of applications, including but not limited to high-precision ranging, robotic vision, automated production, efficient non-linear frequency conversation including harmonic generation (second harmonic, third harmonic, fourth harmonic, sum frequency generation, OPO, etc.), environmental monitoring, micromachining, spectroscopy, cosmetics and microsurgery, skin treatment, ionization spectroscopy, automobile engine ignition, and super continuum generation where the high peak power is required.

The fractional handpiece may be adapted to be applied to the skin of a patient and slide over the skin. In some examples, the fractional handpiece may hover over the skin of the patient and moved at a generally equidistant distance from the surface of the skin. The beam splitting assembly may be operable to generate an array of laser beams across a segment of skin and/or to scan a laser beam emitted by the passively Q-switched laser assembly across a segment of skin. The beam splitting assembly may provide a one-dimensional (1-D) or a two-dimensional (2-D) treated skin area coverage. For example, the beam splitting assembly may generate a fractionated microdot line beam pattern. In some examples, the passively Q-Switched laser handpiece may contain a second or higher order harmonic generator to generate an additional laser wavelength.

Passively Q-Switched Laser Assembly

Passively Q-switched microcavity lasers with cavity lengths of about 10 mm or shorter have been investigated extensively for several decades. However, most studies reported generation of less than a few millijoule pulse energy and less than 10 MW peak power. In particular, some of the lasers were only capable to produce nanosecond laser pulse duration. Most recently, it was demonstrated the generation of 12 mJ from a Yb:YAG/Cr:YAG microchip laser. However, only ~3.7 MW peak power was achievable due to longer pulse duration (1.8 ns). Furthermore the laser had to be operated under cryogenic condition (i.e., 77 degrees K) which makes practical application problematic.

Single pass pumped passively Q-switched lasers have several limitations. In order to ensure the sufficient absorption of pumping energy in the laser material, the laser medium has to be sufficiently long, however longer laser medium will lead to longer emitted pulse duration. In addition, at some particular pump wavelengths, the unabsorbed pump laser can result in unwanted bleaching of saturable absorber causing failure of Q-switching operation. To overcome these above-mentioned issues, the present disclosure introduces a passively Q-switched laser assembly with double pass pumping. Double pass pumping also facilitates use of the laser medium produced from crystals which are difficult to be doped (i.e., Nd:YAG) or have a weak absorption of laser medium at the available pump laser wavelength. The double pass pumping can be made possible by applying highly reflective dielectric coating on either the output end of laser material or input end passive Q-switch for the cavity configuration where two materials (i.e., laser material and saturable absorber) are separated with a small gap. In case of monolithic configuration, the highly reflective coating is sandwiched in between laser material and saturable absorber, while two materials are bonded together. The double pass pumped short cavity laser supports efficient pump laser absorption and shorter medium length leading to shorter pulse duration as well as a more compact laser layout.

The present disclosure describes a short cavity passively Q-switched laser assembly for producing a sub-nanosecond laser pulse with high peak power exceeding 100 MW. The operation of the laser is based on passively Q-switching, in which a passive component acts as a Q-switcher for sake of compact and low-cost design.

The passively Q-switched laser assembly with double pass pumping offers advantage over that with single pass pumping by generating much shorter pulses due to the shorter laser material used. This is because of the Q-switched pulse duration is roughly proportional to the cavity length. Furthermore, for a crystal with low doping concentration or low absorption at pumping laser wavelength, double pass pumping makes it possible to obtain sufficient pump laser absorption while maintaining shorter crystal length leading to a more compact laser design. The passively Q-switched laser assembly may reduce the cavity length since there is no need to introduce bulky active component(s). In some examples, the passively Q-switched laser assembly may use a highly doped laser material and/or a saturable absorber, resulting in shorter material lengths.

The passively Q-switched laser assembly may include two functional groups: pump lenses and a laser cavity. Pump lenses are operable to direct the pump laser into the laser crystal of the laser cavity with certain spot size. The choice of pumping spot is under the tradeoff between available pumping energy and large spot size. The larger spot size leads to higher energy while requiring higher pumping energy to enable Q-switching. The laser cavity enables passively Q-switching to generate subnanosecond laser pulses. The laser cavity may be a monolithic cavity or a cavity with external cavity mirror(s).

Monolithic Cavity

In a monolithic cavity, the laser medium and saturable absorber are sandwiched with a highly reflective dielectric coating at pumping wavelength and bonded with optical contact by intermolecular forces. The highly reflective dielectric coating supports achieving double passing pumping and avoids unwanted bleaching of a passive Q-switch by unabsorbed pump laser.

Figure 3A:
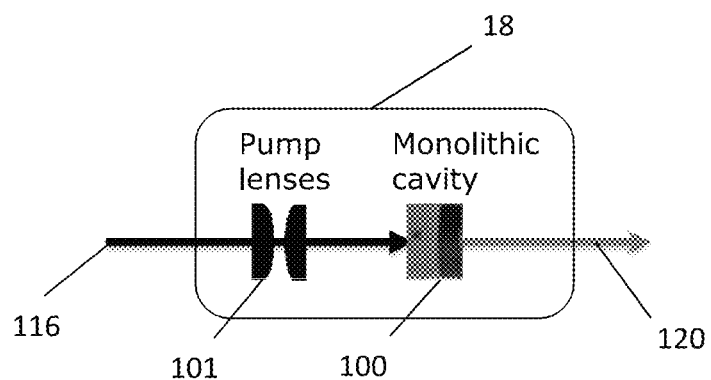
FIG. 3A is an example of a passively Q-switched laser assembly with a monolithic cavity.
Figure 3B:
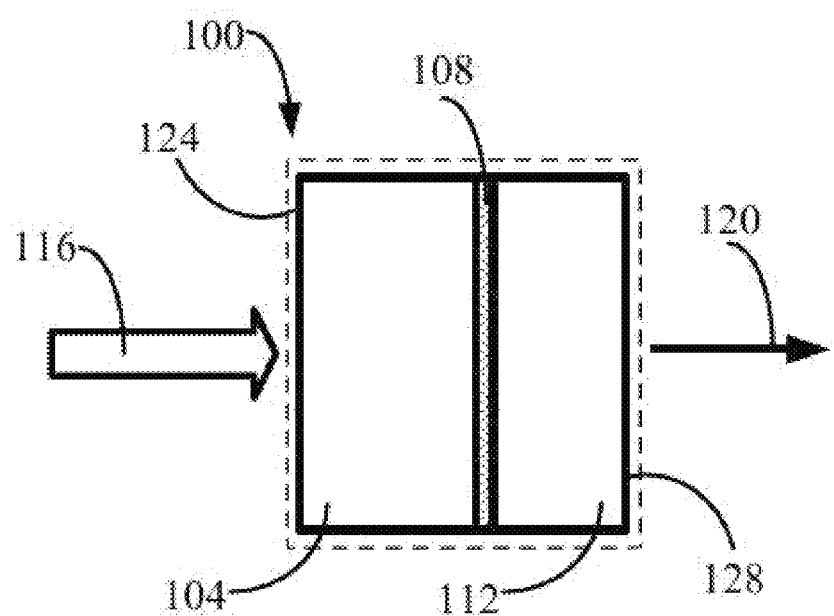
FIG. 3B is an example of a monolithic cavity.

A passively Q-switched laser assembly with a monolithic cavity 100 and pump lenses 101 is shown in FIG. 3A. FIG. 3B shows the monolithic cavity 100 may include a laser medium 104, a highly reflective dielectric coating 108 for pumping laser wavelength sandwiched in between laser medium 104 and a saturable absorber 112. FIGS. 3A and 3B also show a pump laser beam 116 and an output beam 120. The pump laser beam 116 may be, for example a beam with a wavelength of about 755 nm to pump a monolithic microchip laser including Nd:YAG as laser medium and $Cr^{4+}$:YAG as saturable absorber. Highly reflective dielectric coating 108 (highly reflecting at pump laser wavelength, about 755 nm and highly transmitting Q-switched laser wavelength, 1064 nm)) supports achieving double passing pumping and avoids unwanted bleaching of passive Q-switch 112 by unabsorbed pump laser leaking through it. Other pumping wavelengths may be used, including but not limited to diode lasers operating at 800-820 nm, or other types of solid-state emitting laser at about 800-820 nm (i.e., Ti:Sapphire).

At the input end 124 of the monolithic cavity 100, the surface of laser material 104 may be coated with a highly reflective at the laser wavelength (e.g., 1064 nm dielectric coating) and highly transmissive at pump wavelength. At the output end 128 of the monolithic cavity 100, the surface of passive Q-switch 112 may be deposited with dielectric coating partially reflective at the monolithic cavity 100 output beam wavelength. The coating 108 considers the refractive indices of laser medium and saturable absorber such that the coating functions as required when the monolithic material is formed. These two ends (124 and 128) may be arranged to be parallel and coated with dielectric coating, allowing laser oscillation occurs. The two ends may be flat surfaces or curved surfaces with curvatures operable to achieve better mode selectivity.

Diffusion bonding is commonly used to bond laser material and passive Q-switching element (e.g. a saturable absorber) to form passively Q-switched microchip laser. This method is typically accomplished at an elevated pressure and temperature, approximately 50-70% of the absolute melting temperature of the placed in contact materials. Such fabrication process involving elevated temperature and makes it difficult to deposit any form of dielectric coating in between two elements (e.g., laser medium and passive Q-switcher), in particular, highly reflective coating at pump laser wavelength. Therefore, single pass pumping can be only applied.

Figure 4:
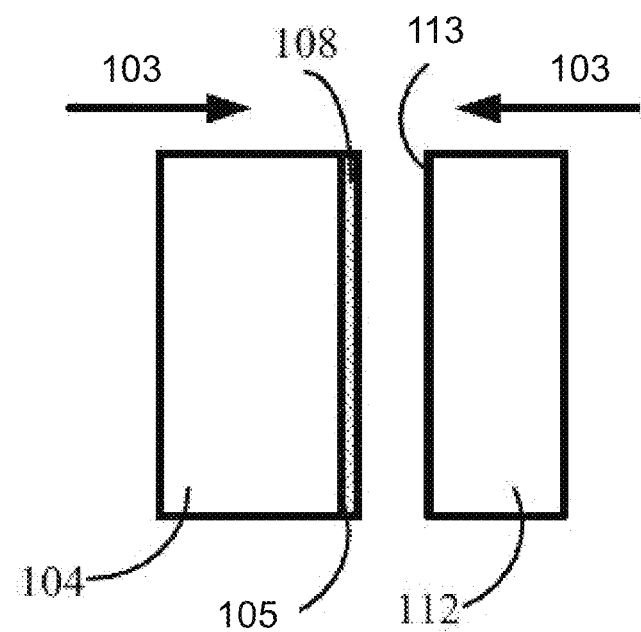
FIG. 4 is an example illustrating the bonding of laser medium and saturable absorber of a microchip laser.

In the current disclosure, the bonding between laser medium 104 and saturable absorber 112 may be implemented as illustrated by arrows 103 through optical contact by intermolecular forces, such as Van der Waals forces, hydrogen bonds, and dipole-dipole interactions, as shown in FIG. 4. No elevated temperature and pressure are needed so that integrity of reflective dielectric coating 108 is protected.

The two surfaces of being contacted i.e., 105 of laser medium 104 and 113 of saturable absorber 112 are processed in optical quality to achieve stable optical contact. The highly reflective dielectric coating at an interface between laser medium 104 and saturable absorber 112 at pump wavelength supports achieving double passing pumping and avoids unwanted bleaching of passive Q-switch by unabsorbed pump laser. Generally, the surface quality may be better than 20-10 scratch-dig. The flatness and roughness may be at least λ/4 10 A rms or better, respectively.

Laser medium 104 may be an Nd doped crystal. The host material may be YAG, YAP, YLF crystals or ceramic. Non-limiting examples of the laser medium include crystals (i.e., Nd:YAG, Nd:YAP, Nd:YLF), or Nd:YAG ceramic. Saturable absorber 112 may be Chromium ($Cr^{4+}$) doped crystals (i.e., YAG) or ceramic YAG. The materials for the laser medium and saturable absorber may be of the same host material or of different materials. In some examples, the laser medium and saturable absorber may be separate ceramic crystals Nd:YAG and Cr:YAG or monolithic composited ceramic crystals Nd:YAG and Cr:YAG. This is quite different from the existing microchip lasers bonded through diffusion methods where the material physical properties (i.e., melting point, thermal expansion coefficient, etc.) for the two components should be similar.

The high energy/high peak power ultrashort pulse microchip laser facilitates efficient non-linear frequency conversation including harmonic generation (second harmonic, third harmonic, fourth harmonic, sum frequency generation, OPO, etc.) and super continuum generation where the high peak power is required. In contrast to the existing low energy microchip laser, the high energy microchip laser can provide higher energy/power at frequency converted wavelengths therefore significantly increase measurement precision by improving signal to noise ratio. Most importantly, the optical arrangement is very compact and simple and supports mounting of the microchip laser in constrained space for example, in a handpiece.

Cavity with External Mirrors

In a cavity with external mirrors, the laser cavity is configured to be a linear cavity with a cavity length shorter than 10 mm for achieving compactness and short pulse generation. In some examples, the cavity length may be less than 10 mm, less than 8 mm, or less than 5 mm. The laser cavity is intended to generate a sub-nanosecond pulsed laser beam. The sub-nanosecond laser pulse may be less than 1000 ps. In various examples, the sub-nanosecond laser pulse may be range from 150 ps to less than 1000 ps, about 200 ps to about 400 ps, about 300 ps to about 500 ps, about 400 ps to about 600 ps, or about 500 ps to about 1000 ps. The sub-nanosecond laser may have a wavelength of about 1 μm (i.e., 1064 nm for Nd:YAG, 1080 nm for Nd:YAP, 1047/1053 nm for Nd:YLF).

A passively Q-switched laser assembly 18 with at least one external mirror laser cavity 200 and pump lenses 101 is shown in FIGS. 5A-5F. The external mirror laser cavity can include one or more external cavity mirrors. In at least one example, the laser cavity may include two external cavity mirrors.

Figure 5A:
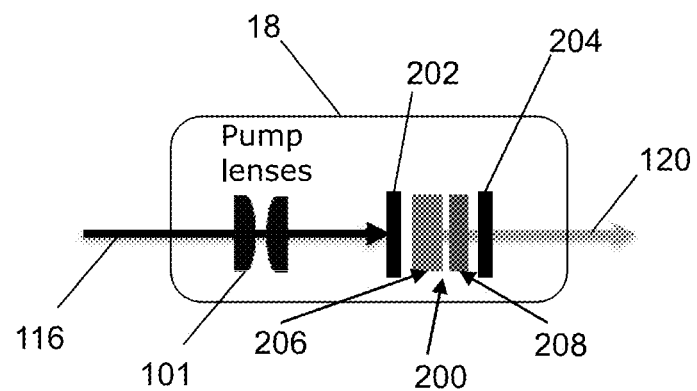
FIG. 5A is an example of a passively Q-switched laser assembly with a cavity with two external cavity mirrors.

In particular, FIG. 5A shows the external mirror cavity 200 may include a pair of cavity mirrors forming resonator (i.e., high reflector (HR) 202 and output coupler (OC) 204), a gain medium 206, and a saturable absorber 208 acting as a passive Q-switcher. Also shown in FIGS. 5A-5F is a pump laser beam 116 and an output beam 120. The pump laser beam 116 may be, for example a beam with a wavelength of about 755 nm. Other pumping wavelengths may be used, including but not limited to diode lasers operating at 800-820 nm, or other solid-state emitting lasers at 800-820 nm (e.g., Ti:Sapphire).

Figure 5B:
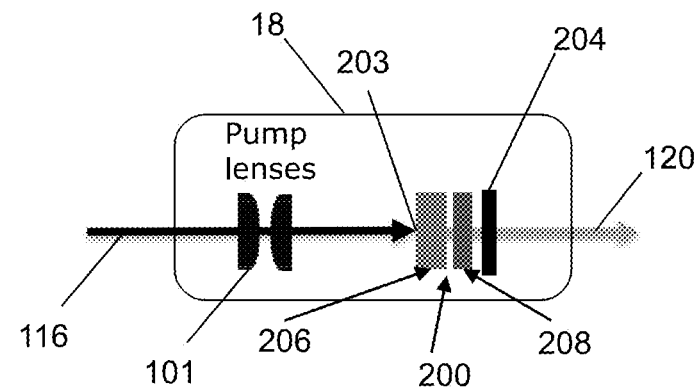
FIG. 5B is an example of a passively Q-switched laser assembly with a cavity with one external cavity mirror (output coupler)
Figure 5C:
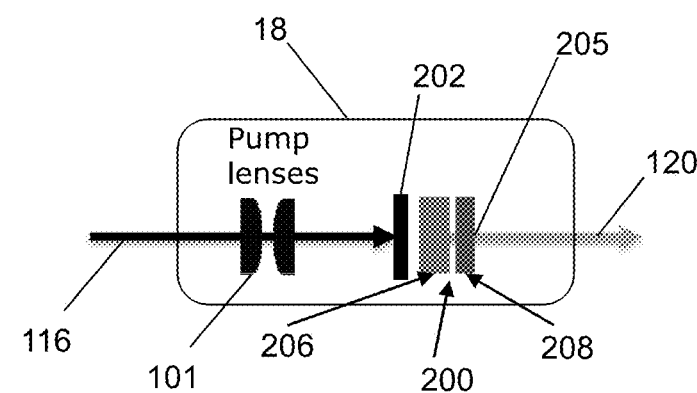
FIG. 5C is an example of a passively Q-switched laser assembly with a cavity with one external cavity mirror (high reflector)

In some other examples, one of the cavity mirrors (i.e., high reflector 202 or output coupler 204) may be replaced by depositing appropriate optical coatings on one of the end surfaces of laser gain medium 206 or saturable absorber 208 (see FIGS. 5B-5C and 5E-5F). The use of only one external cavity mirror may help reduce the cavity length, leading to shorter pulse generation. In one example, a high reflecting coating 203 may be deposited onto the input end of the laser gain medium 206 to act as high reflector while leaving output coupler 204 as one external mirror (FIG. 5B). In another example, only an external high reflector 202 may be included while a partially reflective coating 205 may be deposited onto the output end of the saturable absorber to perform the function of an output coupler (FIG. 5C).

Figure 5D:
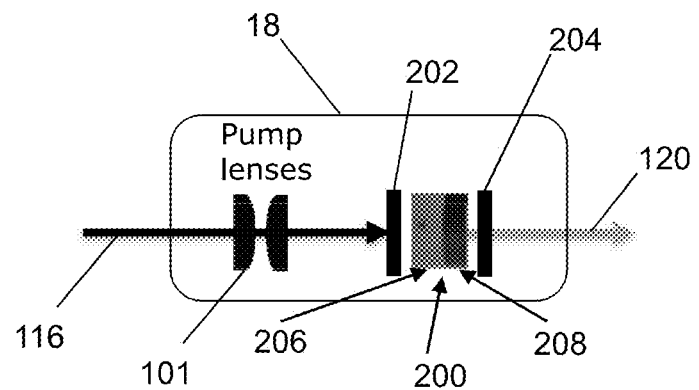
FIG. 5D is an example of a passively Q-switched laser assembly with a cavity formed by one monolithic rod and two external cavity mirrors.
Figure 5E:
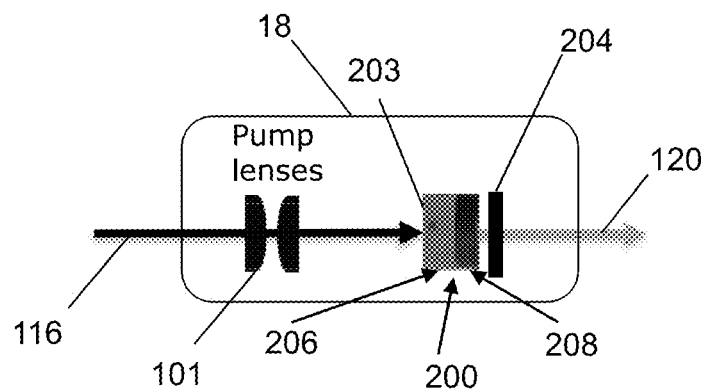
FIG. 5E is an example of a passively Q-switched laser assembly with a cavity formed by a monolithic rod and one external output coupler.
Figure 5F:
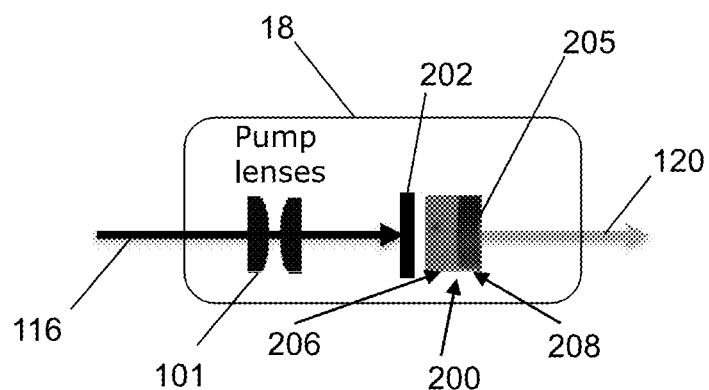
FIG. 5F is an example of a passively Q-switched laser assembly with a cavity formed by one monolithic rod and one external high reflector.

In some examples, laser gain medium 206 can be bonded with saturable absorber 208 as one physical element for shortening cavity length, leading to shorter pulse duration, as seen in FIGS. 5D-5F. Different from the typical monolithic cavity, this monolithic element is coated with AR coatings at laser wavelength on both ends. In addition, the coatings on the input end of this monolithic crystal may be highly transmissive at pump laser wavelength. Similar to the typical monolithic cavity, the laser medium and the saturable absorber are sandwiched with coatings which are highly reflective at the pump wavelength (i.e., first wavelength) and highly transmitting at the laser wavelength (i.e., second wavelength). In various examples, the high reflective coating 203 may be deposited onto the input end of the laser gain medium 206, acting as high reflector while a separate mirror with partially reflective coating acting as an output coupler 204 (FIG. 5E). In other examples, the saturable absorber 208 output end may be coated with a partially reflective coating acting as output coupler 205 while a separate HR mirror 202 may be present for optimizing cavity alignment (FIG. 5F). All these configurations may help in reducing cavity length, which may support shorter pulse generation and simplify the design.

Instead of using a wavelength tuning element in the cavity, the wavelength selectivity may be implemented with high damage threshold optical surface coatings directly deposited on the end surfaces of the cavity mirrors with specific spectral requirements. The high reflector (HR) cavity mirror 202 may be coated to be highly transmitting at pump laser wavelength and highly reflective at laser wavelength (R≥99%) (e.g., 1064 nm for Nd:YAG). The output coupler (OC) cavity mirror may be coated with a partially reflective coating at laser wavelength.

The laser gain medium 206 may include one or more crystals. In some examples, the laser gain medium may be a laser crystal or a ceramic material. Non-limiting examples of crystals are Nd:YAG (neodymium-doped yttrium aluminum garnet), Nd:YAP (Neodymium doped yttrium aluminum perovskite), or Nd:YLF (neodymium-doped yttrium lithium fluoride). In at least one example, the laser gain medium 206 may be rare-earth ion doped ceramic material, such as ceramic Nd:YAG. The front surface of the laser gain medium 206 may by coated with an anti-reflective coating. The back surface of the laser gain medium 206 may be coated with a highly reflective dielectric coating at pump laser wavelength to support achieving double passing pumping and to avoid unwanted bleaching of passive Q-switch by unabsorbed pump laser. Double pass pumping geometry supports sufficient pump laser absorption and shorter medium length leading to a more compact laser layout and shorter pulse duration.

The saturable absorber 208 may act as a passive Q-switcher to implement Q-switching to generate sub-nanosecond laser pulses near 1 μm. Non-limiting examples of the saturable absorber are a $Cr^{4+}$:YAG crystal, a ceramic $Cr^4$:YAG, GaAs, or a semiconductor saturable absorber.

Second Harmonic Generation Assembly

Figure 6:
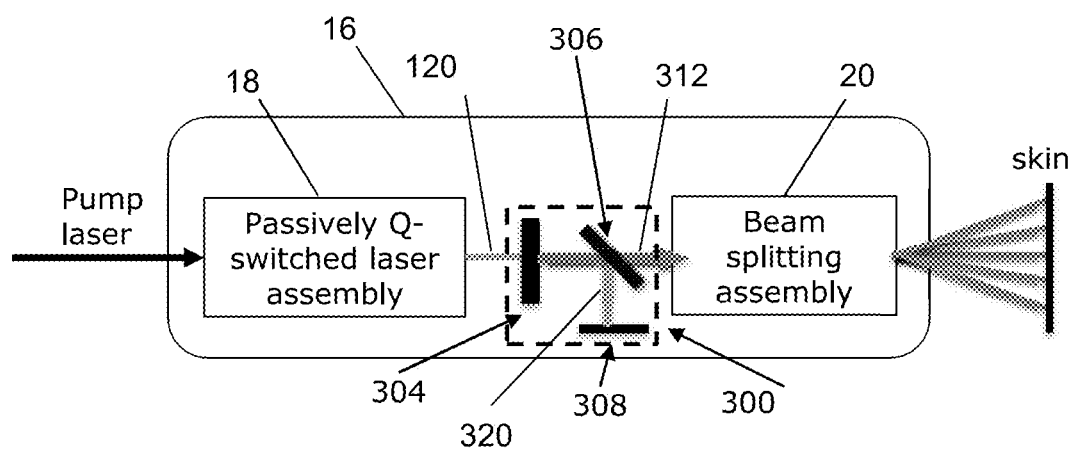
FIG. 6 is an example of a fractional handpiece with a second harmonic generation assembly.

FIG. 6 is an example of a fractional handpiece 16 with a second harmonic generation assembly 300 between the passively Q-switched laser assembly 18 and the beam splitting assembly 20. The laser wavelength out of the passively Q-switched cavity may be converted to other wavelengths through non-linear frequency generation. In some examples, the second harmonic generation assembly 300 may include a frequency doubling crystal 304, a dichroic mirror 306, and a beam dump 308. In an example, the frequency doubling crystal may generate a second harmonic wavelength in the visible wavelength for enhancing melanin absorption.

In some examples, the frequency doubling crystal 304 may be a second harmonic generation crystal (SHG). Non-limiting examples of frequency doubling crystals include lithium niobate ($LiNbO_3$), potassium titanyl phosphate (KTP=$KTiOPO_4$), lithium triborate (LBO=$LiB_3O_5$), or any other SHG crystals. For generation of a stable linearly polarized Q-switched laser, specially cut Nd:YAG (i.e. [100], or/and $Cr^{4+}$:YAG (i.e., [110] cut) may be used.

The dichroic mirror may be operable for transmitting the second harmonic laser while rejecting the residual fundamental wavelength. For example, the frequency doubling crystal 304 receives output beam 120 from the passively Q-switched laser assembly and transforms it into two beams—one beam 320 maintaining the original wavelength (frequency) of the output beam 120 and a beam 312 having a frequency two times higher than the output beam 120. In at least one example, the output beam 120 has a wavelength of 1064 nm, and the beam with the doubled frequency has a wavelength of 532 nm. The dichroic mirror 306 may be a beam splitter that splits and directs beams 320 and 312 in different directions. The beam maintaining the original wavelength 320 may be directed to the beam dump 308. In an example, the beam dump is used to block the rejected fundamental wavelength laser. The output beam of the second harmonic generation assembly 312 may then be passed into the beam splitting assembly 20.

Handpiece

One of potential and promising applications for the passively Q-switched laser assembly producing subnanosecond laser pulses may be in cosmetic and medical laser systems. The high energy short pulse passively Q-switched laser assembly supports packaging of the passively Q-switched laser assembly into a handpiece to perform meaningful aesthetic treatment and in particular fractional skin rejuvenation. It has been demonstrated clinically that for laser pulses of a few hundred picosecond with ~mJ per laser beam is sufficient enough to cause tissue or skin micro-injury through laser induced optical breakdown (LIOB) or melanin assistant optical breakdown. The subsequent collagen remodeling stimulated by such micro-injury will result in skin rejuvenation. The current passively Q-switched laser assembly is capable of generating more than 40 mJ ~300 ps laser pulses with wavelength of 1064 nm. Therefore, the output energy from the passively Q-switched laser assembly can be split into a plurality of micro-beams using a beam splitting assembly 20. For example, the beam from the passively Q-switched laser assembly may be split into at least 2 micro-beams, at least 5 micro-beams, at least 10 micro-beams, at least 15 micro-beams, or at least 30 micro beams. Other numbers of micro-beams are contemplated. Each micro-beam may have up to 4 mJ of laser energy which is sufficient for effective skin treatment for the case of 10 micro-beams. Each of the micro-beams may be focused by a lens in the beam splitting assembly to generate a plurality of micro-dots.

Skin treatment usually requires irradiation of a two-dimensional skin area. Fractional skin treatment may use micro-beams or fractional beams with scanning mirrors or other scanning means. There are a number of approaches to implement two-dimensional micro-beam patterns. For example, the laser beam may be split into a one-dimensional array of micro-beams and the one-dimensional array of micro-beams may be manually slid over the skin. Another approach may use a scanning system to scan the array of micro-beams in one or two direction/axes.

Figure 7A:
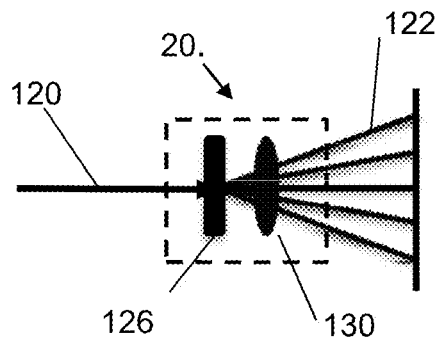
FIG. 7A is an example beam splitting assembly.

FIG. 7A shows an example 1-D beam splitting assembly 20 with a 1-D beam splitter 126 and a focusing lens 130. The beam splitting assembly 20 is designed to split the incoming one solid beam 120 into an array of multiple micro-beams 122 with a combination of the 1-D beam splitter 126 and the focusing lens 130. In some examples, the 1-D beam splitter may be a 1-D diffractive optical beam splitter or a scanner.

The micro-beam size in the focal plane may be in the range of about 10 μm to about 300 μm in diameter. In various examples, the micro-beam size may be up to 10 μm, up to 20 μm, up to 50 μm, up to 100 μm, up to 150 μm, up to 200 μm, up to 250 μm, or up to 300 μm in diameter. In some examples, the micro-beam may have a diameter in the focal plane ranging from about 10 μm to about 50 μm, about 25 μm to about 75 μm, about 50 μm to about 100 μm, about 75 μm to about 125 μm, about 100 μm to about 150 μm, about 125 μm to about 175 μm, about 150 μm to about 200 μm, about 200 μm to about 250 μm, or about 250 μm to about 300 μm.

Figure 7B:
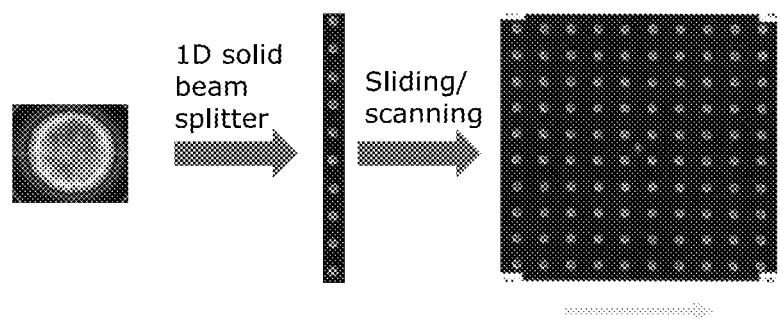
FIG. 7B is an example output of a 1-D solid beam splitter and a resulting scan of the micro-dot array.
Figure 7C:
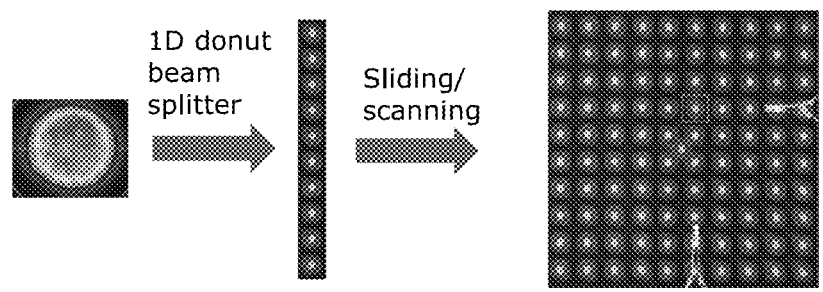
FIG. 7C is an example output of a 1-D donut beam splitter and a resulting scan of the micro-dot array.

The split beam may be solid micro-dot or donut shape (i.e., dot surrounded with a ring). For example, the 1-D beam splitting assembly may include an axicon diffractive optic to form a ring or donut shaped beam, a 1-D beam splitter, and a focusing lens. FIG. 7B shows an example output of a 1-D solid beam splitter and a resulting scan of the micro-dot array. FIG. 7C shows an example output of a 1-D donut beam splitter and a resulting scan of the micro-dot array. The donut shaped beam array help increase surface coverage to reduce the number of passes for treatment.

Figure 7D:
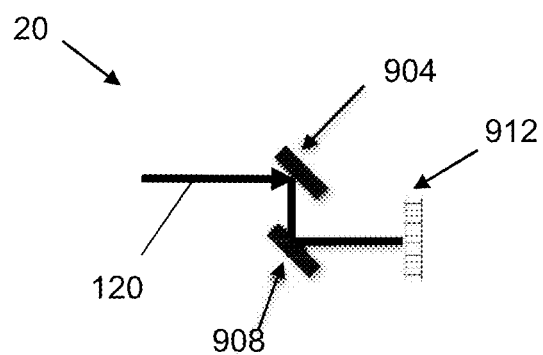
FIG. 7D is an example of a 2-D microbeam pattern generated with the combination of a pair of scanning mirrors and a lens array.
Figure 7E:
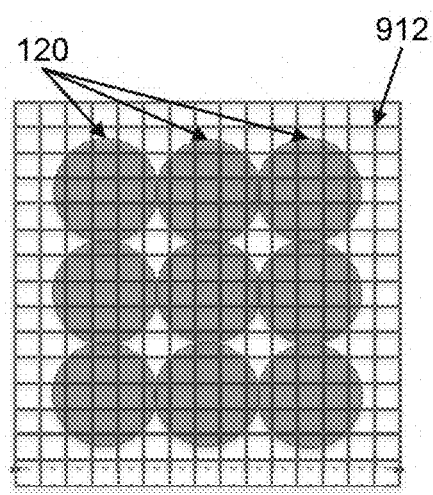
FIG. 7E is an example of subnanosecond laser beams incident on a microlens array with a pair of scanning mirrors
Figure 7F:
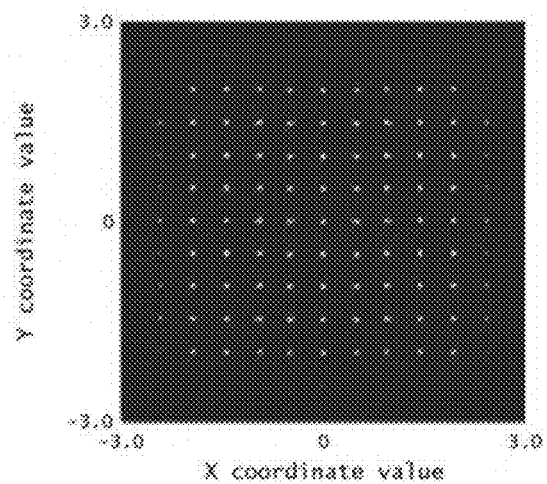
FIG. 7F is an example of 2-D microbeam pattern generated with the setup shown in FIG. 7D.

In other examples, the subnanosecond laser generated from the passively Q-switched laser assembly may be directed to a lens array to form fractionated microbeams by a pair of scanning mirrors. FIG. 7D shows an example beam splitting assembly 20 with a pair of scanning mirrors, e.g. galvanometer driven mirrors (Galvo mirrors) 904 and 908 that project or scan laser beam 120 onto a lens array 912. In some examples, a first scanning mirror 904 may provide in-plane rotation and a second scanning mirror 908 may provide out of plane rotation, while lens array 912 splits laser beam 120 into a plurality of fractionated micro-beams. The combination of a pair of scanning mirrors and lens array optic may generate microdot array with large surface coverage. The movement of two scanning mirror can direct the incident beam across the lens array surface in 2-dimensions to increase surface coverage. To avoid the overlap of the scanning spots or leave spare untreated area, the scanning may be appropriately programmed so that the spots projected on the lens array after one scanning cycle are next to each other. In at least one example, passively Q-switched laser energy is high enough so that each laser beam from the subnanosecond laser can cover multiple lenslets to generate multiple micro-dots with sufficient energy per microdot for meaningful treatment. The scanning mirror pair may scan the laser beam to form a 2-D pattern and cover a larger area of lenslets, as shown in FIG. 7E. After the scanning system completes one cycle, a 2-D micro-dot array may be generated in the skin with larger surface coverage, as seen in FIG. 7F. The scanning of the incident subnanosecond laser beam may be in sequence or in random order.

Figure 8A:
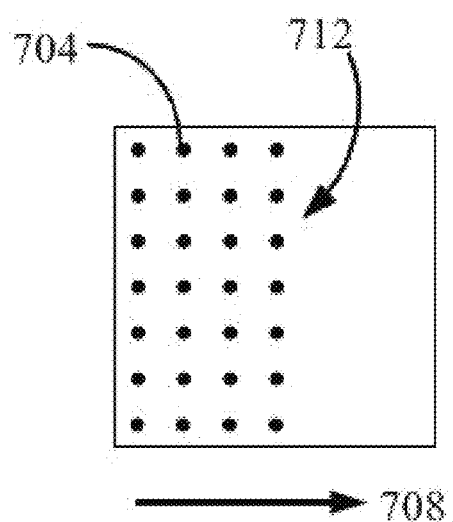
FIG. 8A is an example of a sparse fractional skin treatment pattern.
Figure 8B:
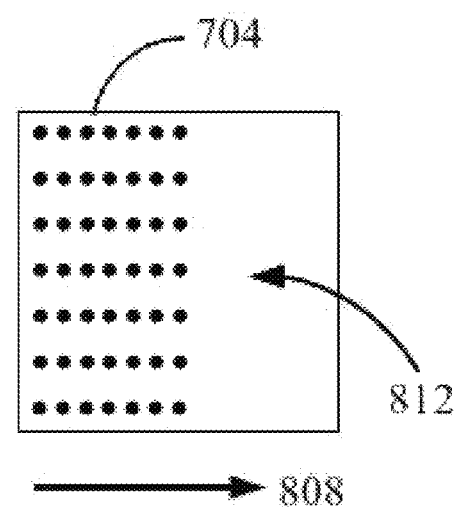
FIG. 8B is an example of a denser fractional skin treatment pattern.

For 1-D beam splitting, the speed of scanning may affect the density or coverage of the micro-dot array across the treatment area. The generated line of multiple micro-beams may be extended to a two dimensional micro-beam array by manually sliding the handpiece along the direction perpendicular to the line of the micro-dots guided with one or two rollers or scanning the line of microdots with a scanner. For example, as seen in FIG. 8A, manual movement of the fractional handpiece in a direction perpendicular to the 1-D fractionated micro-dot line 704 as shown by arrow 708 may generate a 2-D fractional beam pattern 712. The fractional treated skin area coverage may be changed by varying the number of fractionated micro-dots 704 in a 1-D line and/or movement speed of the fractionated handpiece. The movement speed of the fractionated handpiece may determine the spacing between multiple micro-dot arrays. FIG. 8A is an example of a relatively sparse fractionated micro-dot 704 array in a 1-D line (e.g. 7 micro-dots) moved at speed 708. FIG. 8B is an example of the same density fractionated micro-dot 704 array in a 1-D line moved at speed 808. For example, movement speed 708 in FIG. 8A is faster than the same handpiece with movement speed 808 in FIG. 8B. Accordingly, a denser 2-D pattern 812 of fractionated micro-dots 704 is generated. Slower sliding may therefore result in higher coverage of the fractionated beam and faster sliding may result in lower coverage of the fractionated beam over the treatment area. In some examples, the number of fractionated micro-dots in a 1-D line may be adjusted by changing the beamsplitter. For example, the beamsplitter may be a snap-on disposable optic tip operable to connect to the handpiece. Snap-on tips may allow routine easy cleaning of the beamsplitter optics and offer the user different tip designs including different attenuation levels, and different micro-dot arrangements (more or less micro-dots per column, and different micro-dot densities). The user may select different tips based on the number of micro-dots desired per column or same number of micro-dots but with denser or less dense micro-dots.

Figure 9A:
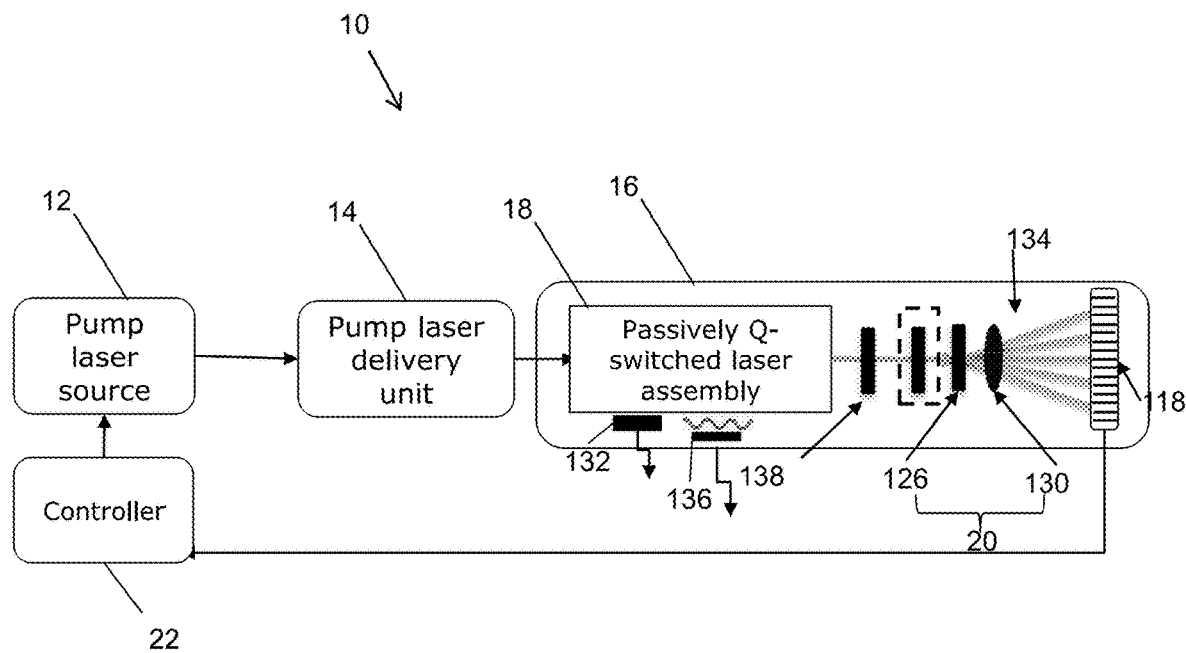
FIG. 9A is an example of laser system with a fractional handpiece with a roller for fractional skin treatment.
Figure 9B:
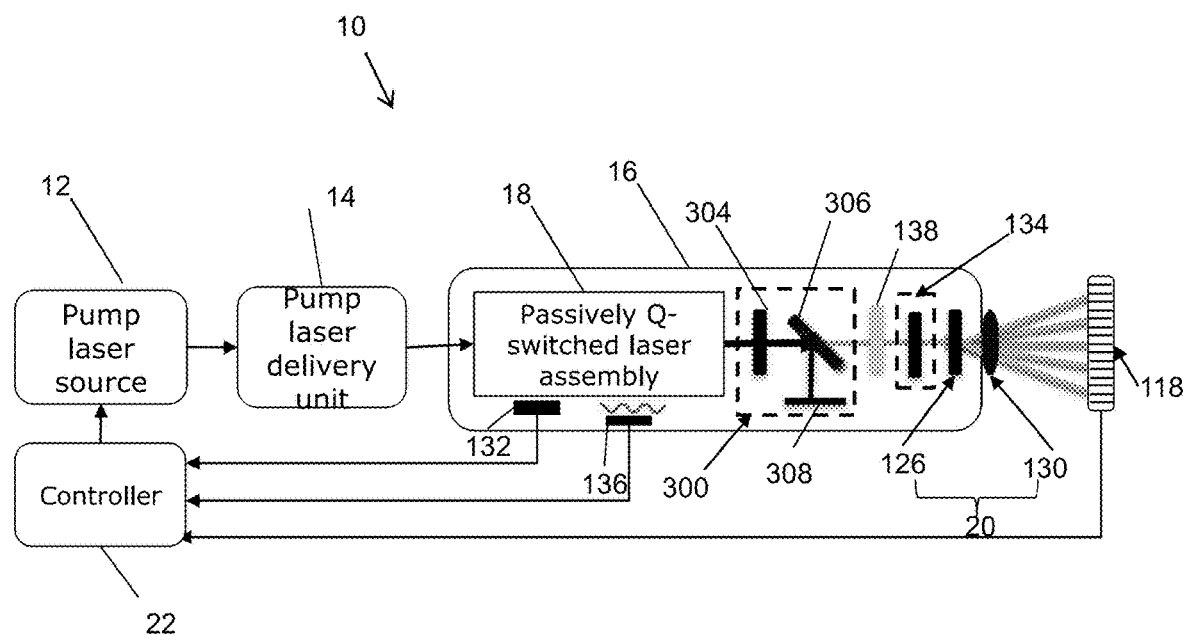
FIG. 9B is an example of laser system with a fractional handpiece with second harmonic generation and a roller for fractional skin treatment.
Figure 10:
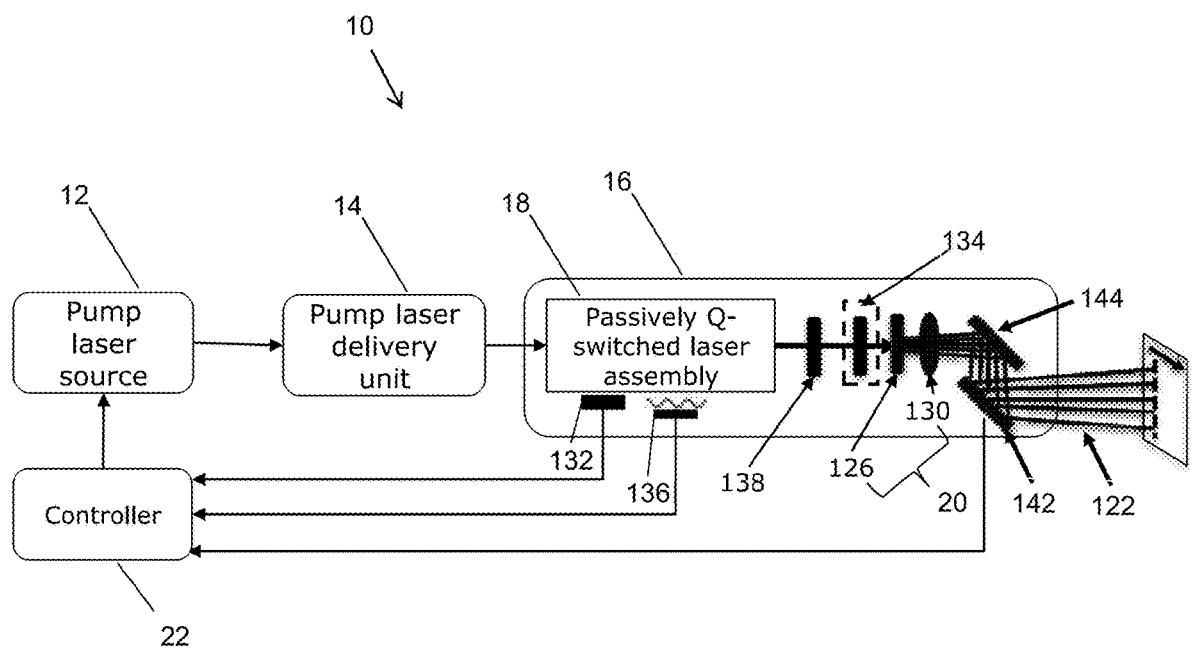
FIG. 10 is an example of laser system with a fractional handpiece with a scanning mirror for fractional skin treatment.

FIGS. 9 and 10 show example fractional handpieces with 1-D beam splitters in the beam splitting assembly 20 that are operable for manual movement of the handpiece. For skin treatment, the caregiver or user may manually slide the fractional handpiece with a 1-D beam splitter over the treated skin area. The fractional handpiece may physically contact the skin or may be at a distance above the surface of the skin as the user slides the handpiece over the patient's skin. In the course of the sliding movement, the passively Q-switched laser assembly may generate subnanosecond laser pulses forming a 1-D fractionated micro-dot line.

In some examples, the fractional handpiece may include one or more positional rollers for manual movement of the handpiece along a direction perpendicular to the 1-D fractionated micro-spot line to form a 2-D micro-spot pattern. The rollers may be used to determine when the pump laser should be fired again. For example, as the 1-D array is moved across the skin, the rollers may track the distance the handpiece has moved and signal to the pump laser source to fire again after the handpiece has moved a set distance. The set distance may range from about 400 µm to about 800 µm. For example, the set distance may be about 400 µm, about 500 µm, about 600 µm, about 700 µm, or about 800 µm. The rollers may also be used as a safety feature, such that when the roller stops, the pump laser source stops. This may prevent tissue damage if the movement of the handpiece is stopped or paused. Alternatively, the laser may be set to fire at a constant rate, and the rollers used to measure the speed of the handpiece movement across the skin surface. The user may receive feedback from the roller if the speed is too fast or too slow. For example, feedback may include lights, different color lights, or tactile vibrations that are initiated when improper scan speeds are triggered.

FIG. 9A is an example of a system with a fractional handpiece with one or two rollers 118 to guide the handpiece movement and to synchronize with laser pulsing. The one or two rollers may be operable for manually sliding the fractional handpiece over a target area. Manually sliding the fractional handpiece may generate a 2-D fractional beam pattern guided by the one or two rollers. The fractional coverage may be changed by varying sliding speed. Slower movement leads to higher surface coverage.

The system 10 may include a pump laser source 12, a pump laser delivery unit 14, a fractional handpiece 16, and a controller 22. As described above, the fractional handpiece 16 may include a passively Q-switched laser assembly 18 and a beam splitting assembly 20, which include a 1-D beam splitter 126 and a focusing lens 130.

The fractional handpiece 16 may further include a fast photodetector 132 or some other means of sensing the sub-nanosecond laser pulse. In an example, the photodetector may communicate with the controller to shut down the pump laser to avoid double or multiple pulsing. In an example, laser pulsing may be synchronized with roller rotation. In some examples, a homogenizer 134 (either diffractive based or refractive based) may be added to the fractional handpiece before the beam splitting array to correct the beam characteristics changes at different repetition rates. The fractional handpiece may also include a vibrator 136, buzzer, mechano-oscillator, or sound system to warn an operator if there is a malfunction of the laser, such as laser missing fire. In addition, the vibrator may be used to provide tactile feedback to help a user control their scan speed by providing feedback to the user if the sliding speed is too slow or too fast. For example, the handpiece may buzz or shake if it is moving too fast. In additional examples, the fractional handpiece 16 may further include an attenuator 138 to achieve appropriate energy for the treatment of different skin types or LIOB depth. The attenuator may a neutral density filter or polarization based elements (such as polarizer cube). The photodetector 132, the vibrator 136, the roller 118, and/or the pump source laser 12 may be operatively connected to the controller 22. Controller 22 is a functional electronics used to receive the electric signals from roller 118, vibrator 136 and photo sensor 132, process them and provide feedback signal to pump laser source for controlling pump laser on and off. The components of the fractional handpiece may be small enough to be packed into the handpiece 16. Such handpiece 16 may be operable to generate a picosecond laser beam, allowing for fractional treatment for skin rejuvenation.

An optional second or higher harmonic generator 300 may be located in handpiece body 16. FIG. 9B shows an example of the handpiece with second harmonic generator 300. Passively Q-switched laser assembly 18 may emit a beam with wavelength of 1064 nm. When additional laser light wavelength is required, the second harmonic generator 300 may be introduced into the laser beam path to generate an additional laser light wavelength. Generally, other wavelength frequency multiplying devices may be arranged on a turret and used when required. The temperature of second harmonic crystal 304 may be controlled by controller 22 for achieving stable and optimized frequency conversion.

FIG. 10 is an example system with a fractional handpiece with a scanning mirror. In some examples, the scanning mirror may be synchronized with laser pulsing. The system 10 may include a pump laser source 12, a pump laser delivery unit 14, a fractional handpiece 16, and a controller 22. As described above, the fractional handpiece 16 may include a passively Q-switched laser assembly 18 and a beam splitting assembly 20, which include a 1-D beam splitter 126 and a focusing lens 130.

The beam splitting assembly may further include a fixed mirror 144 and a rotational mirror 142 which scans a line of micro-beams 122 to form a 2-D micro-spot pattern. The fractional coverage can be changed by varying scanning speed of the rotational mirror 142. In an example, the rotational mirror may be a galvo-mirror operable for out of plane rotation.

The fractional handpiece 16 may further include a fast photodetector 132 or some other means of sensing the sub-nanosecond laser pulse which shuts down the pump laser and avoids double or multiple pulsing. In an example, laser pulsing may be synchronized with rotational mirror rotation. In some examples, a homogenizer 134 (either diffractive based or refractive based) may be added to the fractional handpiece before the beam splitting assembly to correct the beam characteristic changes at different repetition rates. The fractional handpiece may also include a vibrator 136, buzzer, mechano-oscillator, or sound system to warn an operator if there is a malfunction of the laser, such as laser missing fire. In additional examples, the fractional handpiece 16 may further include an attenuator 138 to achieve appropriate energy for the treatment of different skin types or LIOB depth. The attenuator may a neutral density filter or polarization based elements (such as polarizer cube). The photodetector 132, the vibrator 136, the roller 118, and/or the pump source laser 12 may be operatively connected to the controller 22, as described above. The components of the fractional handpiece may be small enough to be packed into the handpiece 16. Such handpiece 16 may be operable to generate a picosecond laser beam, allowing for fractional treatment for skin rejuvenation.

Figure 11:
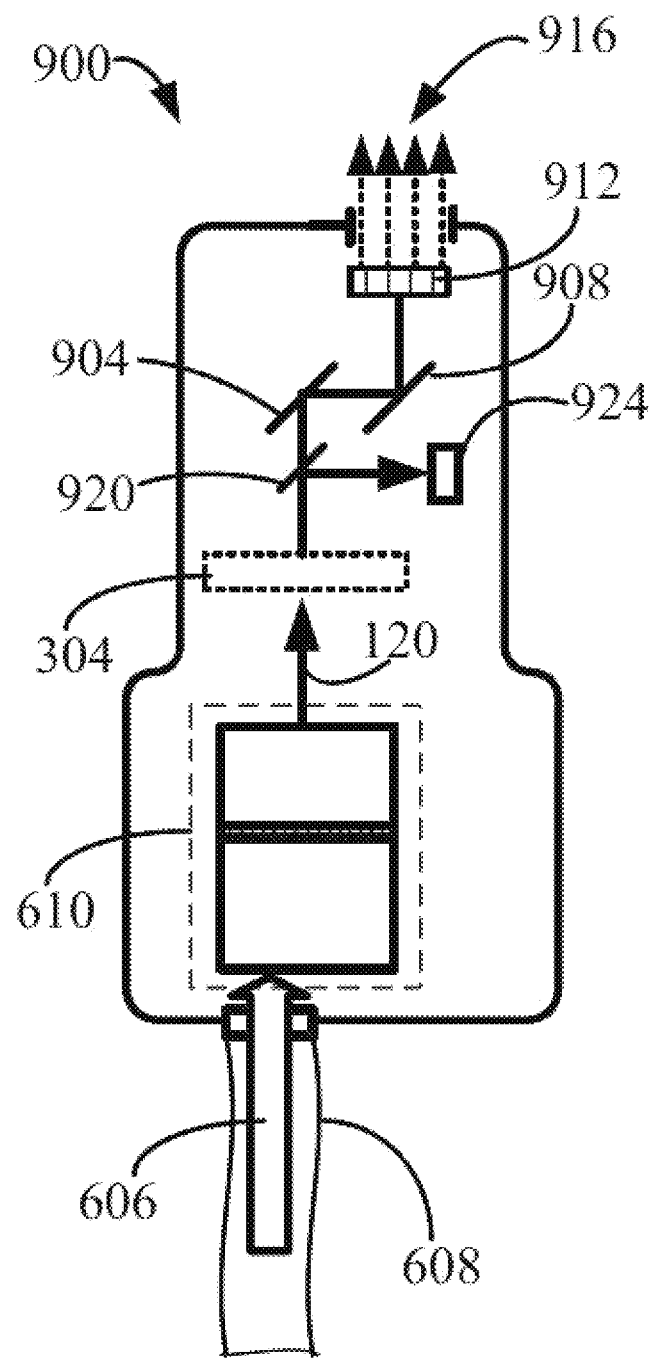
FIG. 11 is another example of a fractional handpiece for fractional skin treatment.

In a further example illustrated in FIG. 11, a handpiece for fractional skin treatment is shown, where the passively Q-switched laser assembly includes a monolithic cavity 610. Generation of a fractionated beam pattern is produced by a combination of a pair of galvo mirrors 904 and 908 that project or scan laser beam 120 onto a lens array 912. Lens array 912 splits laser beam 120 into a plurality of micro-beams 916 which may be fractionated micro-beams. Mirror 920 may be used to separate additional wavelengths generated by the second or higher harmonic generator 304. The coating of mirror 920 is formed accordingly to the desired wavelength separation. The unconverted infrared light 120 may be directed and absorbed in a laser light beam dump 924 while the harmonics may be delivered to the treated skin segment containing a combination of skin disorders. Laser light beam dump 924 may be operable to effectively dissipate the unconverted infrared energy without getting damaged or causing a rise in temperature of other handpiece 900 components. Passive and active cooling mechanisms can be used as need to remove heat from the laser light beam dump 924.

The example below provides some operational parameters of a typical handpiece used for skin disorders treatment. Energy for the output laser 120 of the passively Q-switched laser assembly may be 40 mJ or more. Energy for each micro-beam 122 may be up to 4 mJ at 1064 nm and 2 mJ at 532 nm.

Such laser energy is high enough so that each laser beam from the passively Q-switched laser assembly can cover at least 9 lenslets to generate 9 micro-dots. Galvo mirror pair 904 and 908 scans the laser beam nine times to form a 2-D pattern and cover at least 81 lenslets. Assuming that microchip laser operates at a frequency of 20 Hz, each scan will take 0.45 seconds (9/20) or the treatment can be operated up to 2.2 Hz.

Further provided herein are methods for skin treatment. The method may include delivering a sub-nanosecond pulsed laser beam to a patient in need thereof using the laser system with a fractional handpiece.

Figure 12:
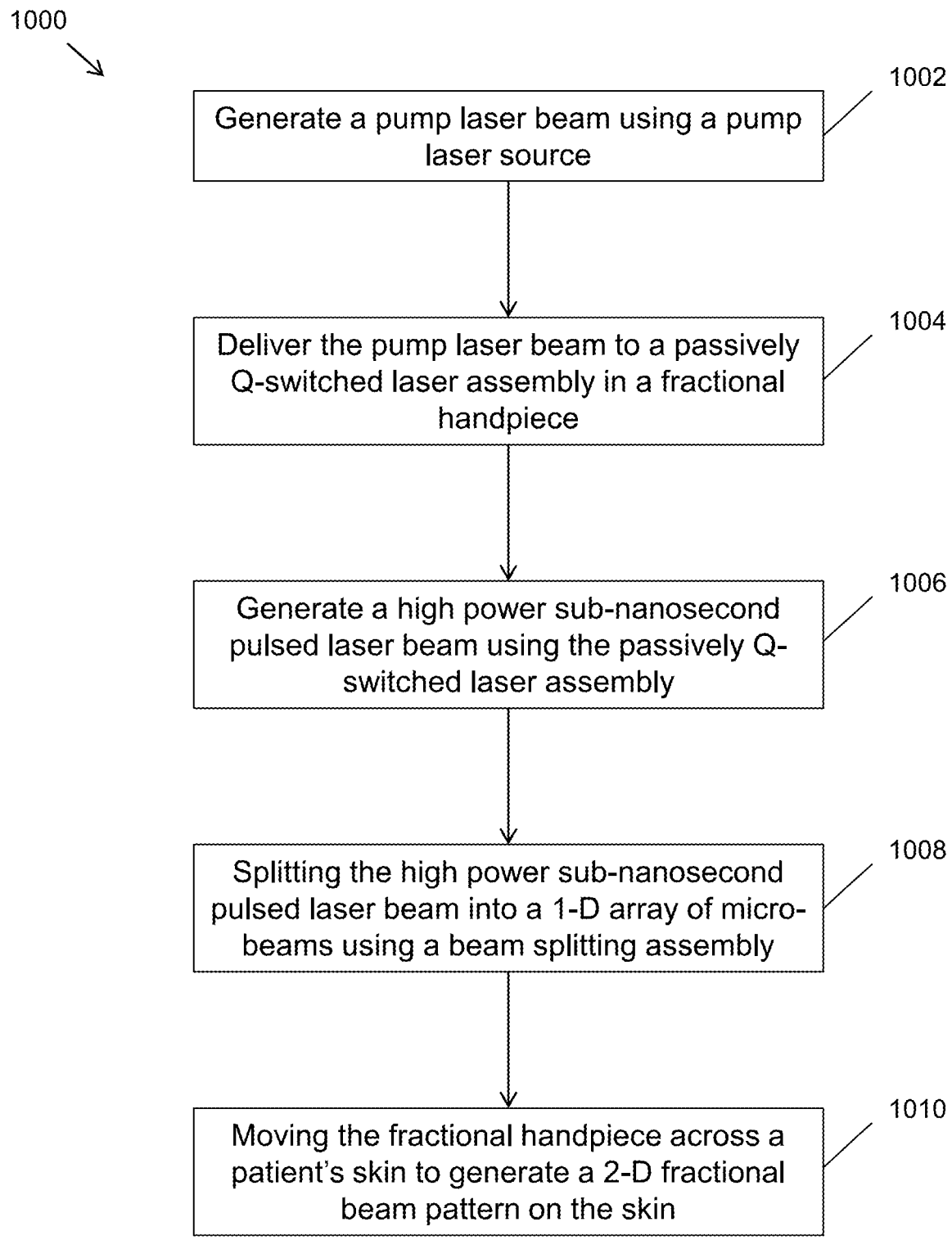
FIG. 12 is a flowchart of an exemplary method of skin treatment by delivering sub-nanosecond laser pulses to a patient in need thereof.

Referring to FIG. 12, a flowchart is presented in accordance with an example embodiment. The method 1000 is provided by way of example, as there are a variety of ways to carry out the method. The method 1000 described below can be carried out using the configurations illustrated in FIGS. 1-11, for example, and various elements of these figures are referenced in explaining example method 1000. Each block shown in FIG. 12 represents one or more processes, methods or subroutines, carried out in the example method 1000. Furthermore, the illustrated order of blocks is illustrative only and the order of the blocks can change according to the present disclosure. Additional blocks may be added or fewer blocks may be utilized, without departing from this disclosure.

The example method 1000 is a method for skin treatment in a patient in need thereof. The example method 1000 can begin at block 1002. At block 1002, a pump laser source generates a pump laser beam at a first wavelength. For example, for an Nd:YAG laser, the pump laser wavelength may be within one of three wavelength bands, i.e., 735-760 nm, 795-820 nm, or 865-885 nm. The pump laser may be a solid state laser or diode laser. Non-limiting examples of pump lasers include an Alexandrite laser (755 nm), a Ti:Sapphire laser, a diode laser, a dye laser, an optical parametric oscillator (OPO), and an optical parameter amplifier (OPA). Ti:Sapphire may be used to generate laser beams in the wavelength range between 700-900 nm via direct emission pumped in the visual wavelength region.

In a non-limiting example, a 755 nm wavelength pump laser beam may be generated from an Alexandrite laser. In another example, a 1.053 μm or 1.047 μm wavelength pump laser beam may be generated from a passively Q-switched Nd:YLF laser.

At block 1004, the pump laser beam is delivered to a passively Q-switched laser assembly in a fractional handpiece. In other examples, the pump laser source may be located within the body of the fractional handpiece and the pump laser beam may directly illuminate the passively Q-switched laser assembly.

At block 1006, the passively Q-switched laser assembly in the fractional handpiece generates a high power sub-nanosecond pulsed laser beam from the pump laser beam. In an example, the generated sub-nanosecond pulsed laser beam has a second wavelength. The second wavelength may be a visible wavelength where melanin has substantial absorption. Some of non-limiting examples include 532 nm, 524 nm, or 528 nm. The sub-nanosecond pulsed laser beam may optionally be delivered to the fractional handpiece via a laser delivery unit.

At block 1008, the sub-nanosecond pulsed laser beam having the second wavelength is split by a beam splitting assembly to form a 1-D array of micro-beams.

At block 1010, the fractional handpiece is moved across the skin to generate a 2-D fractional beam pattern on the skin of the patient. The delivered laser beam may be applied to a target area of the patient's skin. The target area may be on any area of the patient's skin, including but not limited to the face, arm, leg, back, chest, hand, or foot.

It will be appreciated by persons skilled in the art that the present disclosure is not limited to what has been particularly shown and described hereinabove. Rather, the scope of the passively Q-switched laser and handpiece includes both combinations and sub-combinations of various features described hereinabove as well as modifications and variations thereof which would occur to a person skilled in the art upon reading the foregoing description and which are not in the prior art.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

Numerous examples are provided herein to enhance the understanding of the present disclosure. A specific set of statements are provided as follows.

Statement 1: A fractional handpiece for skin treatment comprising: a handpiece body comprising: a passively Q-switched laser assembly within in the handpiece body operatively connected to a pump laser source to receive a pump laser beam having a first wavelength, the passively Q-switched laser assembly comprising one or more pump lenses and a laser cavity comprising one or more external mirrors; and a beam splitting assembly operable to split a solid beam emitted by the passively Q-switched laser assembly and form an array of micro-beams across a segment of skin, wherein the passively Q-switched laser assembly generates a high power sub-nanosecond pulsed laser beam having a second wavelength.

Statement 2: The fractional handpiece of Statement 1, wherein the handpiece body is operable to slide over the skin of a patient.

Statement 3: The fractional handpiece of Statement 1, wherein the pump laser beam at the first wavelength is delivered by an optical fiber or an articulated arm comprising a plurality of arms and mirrors.

Statement 4: The fractional handpiece of Statement 1, wherein the laser cavity comprises a high reflector cavity mirror, an output coupler cavity mirror, a gain medium, and a saturable absorber.

Statement 5: The fractional handpiece of Statement 1, wherein the laser cavity comprises a high reflector cavity mirror, an output coupler cavity mirror, and a gain medium bonded with a saturable absorber and sandwiched with a high reflective coating at the first wavelength and anti-reflective coating at the second wavelength.

Statement 6: The fractional handpiece of Statement 5, wherein an input end of the bonded gain medium is coated with anti-reflective coating at both first and second wavelength while an output end of bonded saturable absorber has anti-reflective coating at second wavelength.

Statement 7: The fractional handpiece of any one of Statements 4 and 5, wherein the high reflector cavity mirror comprises a coating highly transmissive at the first wavelength and highly reflective at the second wavelength.

Statement 8: The fractional handpiece of any one of Statements 4 and 5, wherein the output coupler cavity mirror comprises a partially reflective coating at the second wavelength.

Statement 9: The fractional handpiece of Statement 1, wherein the laser cavity comprises a high reflector cavity mirror, a gain medium, and a saturable absorber, whose output end comprises partially reflective coating at the second wavelength to act as an output coupler.

Statement 10: The fractional handpiece of claim 1, wherein the laser cavity comprises a gain medium with an input end coated with a high transmissive coating at the first wavelength and a high reflective coating at the second wavelength to act as high reflector, a saturable absorber, and an output coupler.

Statement 11: The fractional handpiece of any one of Statements 4-10, wherein the gain medium comprises a laser crystal or a ceramic material.

Statement 12: The fractional handpiece of any one of Statements 4-10, wherein the gain medium comprises Nd:YAG (neodymium-doped yttrium aluminum garnet), Nd:YAP (Neodymium doped yttrium aluminum perovskite), or Nd:YLF (neodymium-doped yttrium lithium fluoride).

Statement 13: The fractional handpiece of Statement 4, wherein the gain medium comprises an anti-reflective coating on a front surface and highly reflective dielectric coating at the first wavelength on a back surface.

Statement 14: The fractional handpiece of any one of Statements 4-10, wherein the saturable absorber comprises a Cr4+:YAG crystal or ceramic Cr4:YAG.

Statement 15: The fractional handpiece of Statement 1, wherein the laser cavity comprises a high reflector cavity mirror and a gain medium bonded with a saturable absorber.

Statement 16: The fractional handpiece of Statement 15, wherein the high reflector cavity mirror comprises a coating highly transmissive at the first wavelength and highly reflective at the second wavelength.

Statement 17: The fractional handpiece of Statement 15, wherein the gain medium is bonded with the saturable absorber and sandwiched with a high reflective coating at the first wavelength and anti-reflective coating at the second wavelength.

Statement 18: The fractional handpiece of Statement 15, wherein an input end of the bonded gain medium is coated with anti-reflective coating at both first and second wavelength while an output end of bonded saturable absorber has a partially-reflective coating at the second wavelength to act as an output coupler.

Statement 19: The fractional handpiece of Statement 1, wherein the laser cavity comprises an output coupler cavity mirror and a gain medium bonded with a saturable absorber.

Statement 20: The fractional handpiece of Statement 19, wherein the output coupler cavity mirror comprises a partially reflective coating at the second wavelength.

Statement 21: The fractional handpiece of Statement 19, wherein the gain medium is bonded with the saturable absorber and sandwiched with a high reflective coating at the first wavelength and an anti-reflective coating at the second wavelength.

Statement 22: The fractional handpiece of Statement 19, wherein an input end of the bonded gain medium is coated with a highly reflective coating at the second wavelength and a highly transmissive coating at the first wavelength to act as a high reflector while an output end of the bonded saturable absorber has an anti-reflective coating at the second wavelength.

Statement 23: The fractional handpiece of Statement 1, wherein the sub-nanosecond laser pulse is less than 1000 ps.

Statement 24: The fractional handpiece of Statement 1, further comprising a scanning system comprising a pair of scanning mirrors to generate two-dimensional microbeam pattern.

Statement 25: The fractional handpiece of Statement 24, wherein a scanned beam incidents on a lens array to form a microbeam array.

Statement 26: The fractional handpiece of Statement 1, wherein the beam splitting assembly comprises a 1-D beam splitter and a focusing lens.

Statement 27: The fractional handpiece of Statement 26, wherein the beam splitting assembly further comprises an axicon diffractive optic to generate donut beam pattern.

Statement 28: The fractional handpiece of Statement 26, wherein the 1-D beam splitter is operable to generate a 1-D fractionated micro-dot line.

Statement 29: The fractional handpiece of Statement 28, further comprising one or more rollers operable to allow manual movement of the handpiece along a direction perpendicular to the 1-D fractionated micro-dot line to form a 2-D micro-spot pattern.

Statement 30: The fractional handpiece of Statement 28, wherein the beam splitting assembly further comprises a fixed mirror and a rotational mirror operable to scan the 1-D fractionated micro-dot line to form a 2-D micro-spot pattern.

Statement 31: The fractional handpiece of Statement 26, wherein the beam splitting assembly is operable to snap on the fractional handpiece.

Statement 32: The fractional handpiece of Statement 31, wherein the beam splitting assembly is disposable.

Statement 33: The fractional handpiece of Statement 1, wherein the handpiece body further comprises a second harmonic generator to generate an additional laser light wavelength.

Statement 34: The fractional handpiece of Statement 1, wherein the handpiece body further comprises a fast photodetector operable to sense the sub-nanosecond pulsed laser beam and to shut down the pump laser to avoid double or multiple pulsing.

Statement 35: The fractional handpiece of Statement 1, wherein the handpiece body further comprises a homogenizer before the beam splitting assembly to mitigate beam characteristic changes at different repetition rates.

Statement 36: The fractional handpiece of Statement 1, wherein the handpiece body further comprises a vibrator operable to vibrate to warn or provide feedback to a user if there is any malfunction of the laser or sliding speed is too slow or too fast.

Statement 37: The fractional handpiece of Statement 1, wherein the handpiece body further comprises an attenuator operable to achieve appropriate energy for treatment of different skin types or LIOB depth.

Statement 38: The fractional handpiece of Statement 1, wherein the handpiece body further comprises one or two rollers to guide movement of the fractional handpiece and to synchronize with laser pulsing.

Statement 39: The fractional handpiece of Statement 1, further comprising a controller.

Statement 40: A laser system comprising: a pump laser source operable to provide a pumping laser beam; and the fractional handpiece of any one of Statements 1-39.

Statement 41: The laser system of Statement 40, wherein the pump laser source is within the fractional handpiece.

Statement 42: The laser system of Statement 40, wherein the pump laser source is a diode laser or an Alexandrite laser.

Statement 43: A method of skin treatment, the method comprising: generating, via a pump beam source, a pump laser beam having a first wavelength; delivering the pump laser beam to a passively Q-switched laser assembly in a fractional handpiece, the passively Q-switched laser assembly comprising one or more pump lenses and a laser cavity comprising one or more external mirrors; generating, via the passively Q-switched laser assembly, a high power sub-nanosecond pulsed laser beam having a second wavelength; splitting, via a beam splitting assembly, the high power sub-nanosecond pulsed laser beam into a 1-D array of micro-beams; and moving the fractional handpiece across a patient's skin to generate a 2-D fractional beam pattern on the skin of a patient in need thereof.

What is claimed is:

1. A fractional handpiece for skin treatment comprising:
  a handpiece body comprising:
    a passively Q-switched laser assembly within in the handpiece body operatively connected to a pump laser source to receive a pump laser beam having a first wavelength, the passively Q-switched laser assembly comprising one or more pump lenses and a laser cavity comprising one or more external mirrors; and
    a beam splitting assembly operable to split a solid beam emitted by the passively Q-switched laser assembly and form an array of micro-beams across a segment of skin, the beam splitting assembly comprising a 1-D beam splitter, a focusing lens, and one or more rollers operable to allow manual movement of the handpiece along a direction perpendicular to a 1-D fractionated micro-dot line to form a 2-D micro-spot pattern,
  wherein the passively Q-switched laser assembly generates a high power sub-nanosecond pulsed laser beam having a second wavelength.

2. The fractional handpiece of claim 1, wherein the laser cavity comprises a high reflector cavity mirror, an output coupler cavity mirror, a gain medium, and a saturable absorber.

3. The fractional handpiece of claim 1, wherein the laser cavity comprises a high reflector cavity mirror, an output coupler cavity mirror, and a gain medium bonded with a saturable absorber and sandwiched with a high reflective coating at the first wavelength and anti-reflective coating at the second wavelength.

4. The fractional handpiece of claim 3, wherein the high reflector cavity mirror comprises a coating highly transmissive at the first wavelength and highly reflective at the second wavelength.

5. The fractional handpiece of claim 3, wherein the output coupler cavity mirror comprises a partially reflective coating at the second wavelength.

6. The fractional handpiece of claim 3, wherein the gain medium comprises Nd:YAG (neodymium-doped yttrium aluminum garnet), Nd:YAP (Neodymium doped yttrium aluminum perovskite), or Nd:YLF (neodymium-doped yttrium lithium fluoride).

7. The fractional handpiece of claim 3, wherein the saturable absorber comprises a Cr4+:YAG crystal or ceramic Cr4:YAG.

8. The fractional handpiece of claim 1, wherein the laser cavity comprises a high reflector cavity mirror, a gain medium, and a saturable absorber, whose output end comprises partially reflective coating at the second wavelength to act as an output coupler.

9. The fractional handpiece of claim 1, wherein the laser cavity comprises a gain medium with an input end coated with a high transmissive coating at the first wavelength and a high reflective coating at the second wavelength to act as high reflector, a saturable absorber, and an output coupler.

10. The fractional handpiece of claim 1, wherein the laser cavity comprises a high reflector cavity mirror and a gain medium bonded with a saturable absorber and sandwiched with a high reflective coating at the first wavelength and anti-reflective coating at the second wavelength.

11. The fractional handpiece of claim 10, wherein the high reflector cavity mirror comprises a coating highly transmissive at the first wavelength and highly reflective at the second wavelength.

12. The fractional handpiece of claim 10, wherein an input end of the bonded gain medium is coated with anti-reflective coating at both the first wavelength and second wavelength while an output end of the bonded saturable absorber has a partially-reflective coating at the second wavelength to act as an output coupler.

13. The fractional handpiece of claim 1, wherein the laser cavity comprises an output coupler cavity mirror and a gain medium bonded with a saturable absorber and sandwiched with a high reflective coating at the first wavelength and anti-reflective coating at the second wavelength.

14. The fractional handpiece of claim 13, wherein the output coupler cavity mirror comprises a partially reflective coating at the second wavelength.

15. The fractional handpiece of claim 13, wherein an input end of the bonded gain medium is coated with a highly reflective coating at the second wavelength and a highly transmissive coating at the first wavelength to act as a high reflector while an output end of the bonded saturable absorber has an anti-reflective coating at the second wavelength.

16. The fractional handpiece of claim 1, wherein the beam splitting assembly further comprises a fixed mirror, and a rotational mirror operable to scan a 1-D fractionated micro-dot line to form a 2-D micro-spot pattern.

17. The fractional handpiece of claim 1, wherein the beam splitting assembly further comprises an axicon diffractive optic to generate donut beam pattern.

18. The fractional handpiece of claim 1, wherein the handpiece body further comprises a second harmonic generator to generate an additional laser light wavelength.

19. A fractional handpiece for skin treatment comprising:
a handpiece body comprising:
a passively Q-switched laser assembly within in the handpiece body operatively connected to a pump laser source to receive a pump laser beam having a first wavelength, the passively Q-switched laser assembly comprising one or more pump lenses and a laser cavity comprising one or more external mirrors, wherein the passively Q-switched laser assembly generates a high power sub-nanosecond pulsed laser beam having a second wavelength; and
a beam splitting assembly operable to split a solid beam emitted by the passively Q-switched laser assembly and form an array of micro-beams across a segment of skin;
wherein the handpiece body further comprises:
a fast photodetector operable to sense the sub-nanosecond pulsed laser beam and to shut down the pump laser source to avoid double or multiple pulsing;
a homogenizer before the beam splitting assembly to mitigate beam characteristic changes at different repetition rates;
a vibrator operable to vibrate to warn or provide feedback to a user if there is any malfunction of the laser or sliding speed is too slow or too fast;
an attenuator operable to achieve appropriate energy for treatment of different skin types or LIOB depth; and/or
one or two rollers to guide movement of the fractional handpiece and to synchronize with laser pulsing.

20. The fractional handpiece of claim 1, wherein the one or more rollers are further operable to synchronize with laser pulsing.

21. The fractional handpiece of claim 1, wherein the handpiece body further comprises a homogenizer before the beam splitting assembly.

* * * * *